US00PP12539P2

(12) United States Plant Patent
Zerr

(10) Patent No.: US PP12,539 P2
(45) Date of Patent: Apr. 9, 2002

(54) POINSETTIA PLANT NAMED 'FISSON PIZ'

(75) Inventor: Katharina Zerr, Höhr-Grenzhausen (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/496,197

(22) Filed: Feb. 2, 2000

(51) Int. Cl.[7] ..... A01H 5/00
(52) U.S. Cl. ..... Plt./307
(58) Field of Search ..... Plt./307, 303

(56) References Cited

U.S. PATENT DOCUMENTS

PP9,365 P * 11/1995 Zerr ..... Plt./307
PP11,368 P * 5/2000 Dummen ..... Plt./307

FOREIGN PATENT DOCUMENTS

CH 00.37.1318 1/2001
DE EUP 215 11/1998

OTHER PUBLICATIONS

UPOV–ROM Computer Database 2001/01, Feb. 6, 2001, GTI Jouve Retrieval Software, Citation for Euphorbia 'Fisson Piz'.*

1999 Fischer USA, Inc. Catalogue.

* cited by examiner

*Primary Examiner*—Bruce R. Campell
*Assistant Examiner*—June Hwu
(74) *Attorney, Agent, or Firm*—Foley & Lardner

(57) ABSTRACT

A new and distinct cultivar of Poinsettia plant named 'Fisson Piz' characterized by having uniform scarlet bract color; medium-sized, flat inflorescence with strongly serrated/slashed/lobed bracts; intense dark-green foliage with very strong dentation; compact and well-branched, round plant habit; and medium to late flowering response in combination with good after-sale keeping quality.

1 Drawing Sheet

BACKGROUND OF THE INVENTION

The present invention relates to a new and distinct cultivar of poinsettia plant known by the cultivar name 'Fisson Piz' and botanically known as *Euphorbia pulcherrima.*

'Fisson Piz' is a product of a mutation induction program carried out by the inventor, Katharina Zerr, in Hillscheid, Germany, in 1994. The primary objective of the induction program was to expand the bract color ranges of 'Fisson' (U.S. Plant Pat. No. 9,365). 'Fisson' is characterized by its intense red-colored bracts with pointed lobes, dark-green foliage and relatively compact habit.

The irradiation program comprised exposing rooted cuttings taken from plants of the parent cultivar to an X-ray source of 30 Gy dosage in Ahrensburg, Germany, under the supervision of the inventor. The irradiated plants were grown out in a greenhouse in Hillscheid, Germany, and were asexually propagated by the inventor by taking cuttings. The plants resulting from these cuttings were screened for mutations as small, flowering, single-stem plants beginning in autumn of 1994 and continuing thereafter. The mutations discovered were identified by numbers. Parts of plants exhibiting a mutation of interest were left to develop vegetative shoots which were used as cuttings and grown out.

'Fisson Piz' originated from a single plant (no. 525) displaying red and orange-red marbled bracts, which was discovered in the late summer of 1995. It was propagated vegetatively by taking cuttings, and among the resulting plants, one plant was selected, the bracts of which had a uniform scarlet color and displayed very strong dentation. Only this plant was propagated vegetatively and formed the base of the new variety. Horticultural examination of the clone starting in 1997 and continuing thereafter has confirmed that the combination of characteristics as herein disclosed for 'Fisson Piz' are firmly fixed and retained through successive generations of asexual reproduction.

BRIEF DESCRIPTION OF THE INVENTION

The following traits have been repeatedly observed and are determined to be basic characteristics of 'Fisson Piz' which in combination distinguish this Poinsettia as a new and distinct cultivar:

1. Uniform scarlet bract color;
2. Medium-sized, flat inflorescence with strongly serrated/slashed/lobed bracts;
3. Intense dark-green foliage with very strong dentation;
4. Compact and well-branched, round plant habit; and
5. Medium to late flowering response in combination with good after-sale keeping quality.

'Fisson Piz' has not been observed under all possible environmental conditions. The phenotype may vary significantly with variations in environment such as temperature, light intensity, and daylength without any change in genotype. The following observations, measurements and comparisons describe plants grown in Langley, British Columbia, Canada, under greenhouse conditions which approximate those generally used in commercial practice.

Of the many commercial cultivars known to the inventor, the most similar in comparison to 'Fisson' are the parental cultivar 'Fisson Piz' and the variety 'Fisson Orange' (U.S. Plant patent application Ser. No. 09/210,121). In comparison to 'Fisson', 'Fisson Piz' has a slightly brighter, scarlet bract color, and even more strongly lobed/dentated bracts and leaves. The reddish anthocyanin coloring of stems and petioles of 'Fisson Piz' is not quite as intense as with 'Fisson'. In comparison to 'Fisson Orange', 'Fisson Piz' has distinctly stronger lobed bracts and leaves.

Due to its narrower bracts, the inflorescence of 'Fisson Piz' appears less massive but form an almost lace-like pattern on the surface of the canopy. For the same reason, the finishing time for 'Fisson Piz' is about 7 days longer than for the two comparison varieties. On the other hand, its bracts do not tend to drooping and therefore have an excellent after-sale quality.

BRIEF DESCRIPTION OF THE DRAWING

The accompanying color photographic illustration shows typical inflorescence and foliage of a mature potted plant of 'Fisson Piz', with colors being as true as possible with illustrations of this type.

DETAILED BOTANICAL DESCRIPTION

The plants described were grown in a greenhouse in Langley, British Columbia, Canada, in the fall of 1998. Rooted cuttings were planted in 15-cm pots (in diameter) on August 10, and were pinched on August 20, leaving 8 nodes. The minimum temperature was 23° C. until October 10, 20° C. to mid-November, and lower thereafter. The plants initiated flowers under natural short-day conditions in the fall. The plants. The age of the plants observed is 15 weeks after planting of rooting cuttings.

Observations and measurements were mainly taken at the beginning of full flowering. In the following description color references are made to The Royal Horticultural Society (R.H.S.) Color Chart. The color values were determined indoors in a north light.

Classification:

*Botanical.*—*Euphorbia pulcherrima.*

*Commercial.*—Poinsettia, cv. 'Fisson Piz'.

Parentage: Induced mutation of 'Fisson'.

Plant:

*Form.*—Shrub, self-branching.

*Growth habit.*—Relatively compact, weak to medium growth, pinched plants are bushy and round in shape.

*Height* (*including 12 cm high pot*).—Approximately 36.9 cm.

*Width.*—45.3 cm.

*Average number of branches.*—10.9.

*Stem color.*—Relatively light-green, RHS 143A–B, with very weak infusion of anthocyanin, light brownish-reddish about RHS 176 C.

*Peduncle.*—Light green, RHS 143C, about 10 mm long.

*Rooting.*—Medium, sufficiently rooted for transplanting after about 20–24 days in a greenhouse at a temperature of 22–24° C.

*Blooming habit.*—Flowering response time under natural short day conditions in autumn: botanically (cyathia open) — around December 1; commercially (bracts colored, marketable) — in early December.

*Flowering response time.*—About 10 weeks.

Foliage:

*Shape.*—Basal part roughly triangular, acute base, acuminate tip, and very strong dentation with pointed lobes.

*Edge of margin.*—Entire, apart from the lobes.

*Texture.*—Upper surface: Smooth, flat and only weakly veined, color of veins is RHS 146 D or lighter; the basal part of the midrib has a similar reddish coloring as the petiole. Lower surface: Flat and smooth, except for the slightly protruding midrib and finer side veins, which protrude at an acute, almost right angle from the midrib; the side veins are evenly spread throughout the leaf blade and run parallel to each other; the vein color is light green, RHS 145C.

*Size.*—Leaf blade length is 9.95 cm; leaf blade width is 8.05 cm; petiole length is 7.5 cm.

*Color.*—Generally a uniform dark green. Mature foliage: Upper surface is dark-green, intermediate between RHS 137A and RHS 139A; under surface is RHS 137B. New foliage: Upper side is about RHS 143A. under side is about RHS 137D.

*Petiole color.*—Brownish-red, near RHS 181A. Aspect: Petioles are horizontally directed, while the leaf blades show slightly downward.

*Disease resistance.*—Typical, no special observations made.

Flowering description:

*Whole inflorescence.*—Flat and horizontally directed; later possibly slightly downward.

*Diameter of inflorescence.*—About 23 cm.

*Keeping quality.*—Good chlorophyll stability, no leaf drop, no fading bract color, commercial quality can be maintained for about 4 to 5 weeks.

*Number of bracts per inflorescence.*—On average 11 bracts.

*Size of bract.*—Largest true bract is 12.7 cm long and 7.8 cm wide; petiole is 1.8 cm.

*Bract shape.*—The basal part of the bracts is roughly triangular, with acute base, very strong lobes with pointed tips, and with acuminate tip.

*Bract texture.*—Flat or slightly folded along the midrib; smooth at the beginning of flowering with the veins hardly visible; the vein color of the upper side corresponds to the bract color, while the veins on the underside are usually lighter: pink, about RHS 54 C.

*Bract color.*—Generally an intense and uniform scarlet-red. Upper surface: RHS 44A–45B. Lower surface: RHS 46C.

*Secondary bract.*—Basal part of bract is roughly triangular, acute base, lobes not as deep as primary bract lobes, upper surface RHS 44A–45B, lower surface RHS 46C; largest secondary bract 12.7 cm long, next largest secondary bract 8.5 cm long.

*Petiole color.*—Red, approximately RHS 46B.

*Cyathia.*—Few, about 8–10 in a narrow cluster, about 20 mm wide. Diameter of the single cyathium: 5–6 mm. Color: Mainly light green, RHS 143C, with darker, medium-green patches, about RHS 137D; top is red, about RHS 45B. Retention: Medium, roughly 3–4 weeks at natural light conditions in December, as described for western Canada or central Europe, longer with additional lighting or in southern areas with higher light intensity in winter. Nectar Cups: Usually one nectar cup per cyathium, small to medium sized, 4 mm diameter, bright yellow, RHS 8A, usually no anthocyanin coloring near the margin.

Reproductive organs:

*Stamens.*—Red filaments, RHS 46B, fertile, yellow pollen, RHS 8A.

*Pistils.*—Style and stigma are red, RHS 46B; style length 3–4 mm; 6-lobed stigma.

*Ovaries.*—Triangular, 3 ovules, green RHS 143A.

Fruit/seed set: No observations made.

I claim:

1. A new and distinct poinsettia plant named 'Fisson Piz', substantially as illustrated and described.

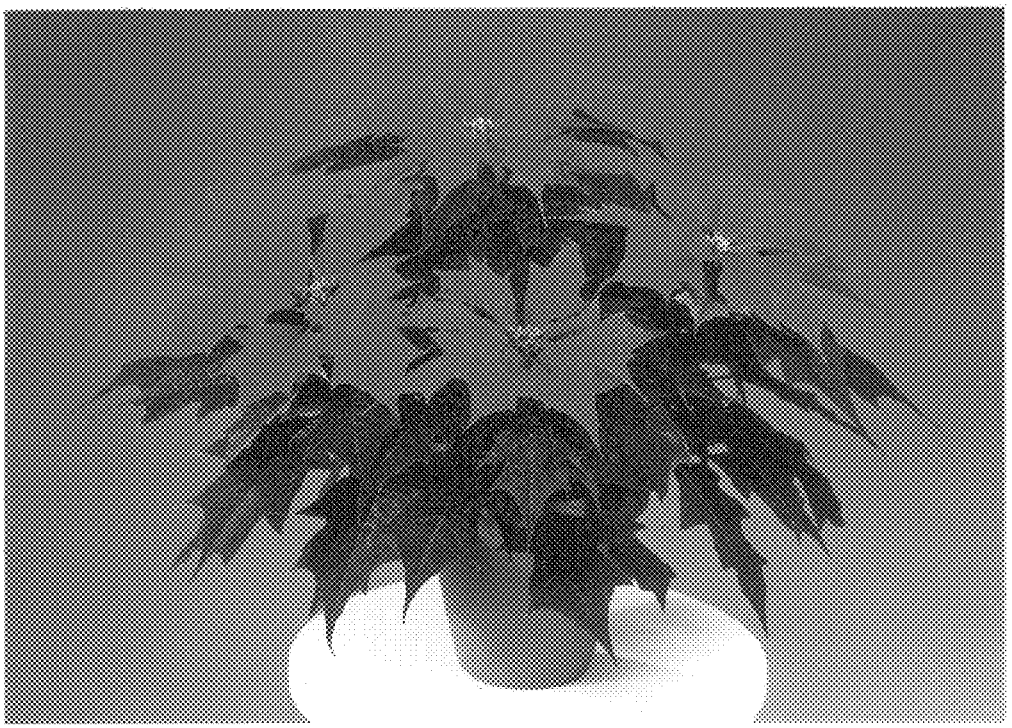

* * * * *